US009683004B2

(12) United States Patent
Pikramenou et al.

(10) Patent No.: US 9,683,004 B2
(45) Date of Patent: Jun. 20, 2017

(54) COATED NANOPARTICLES (75) Inventors: Zoe Pikramenou, Birmingham (GB); Nicola Rogers, Birmingham (GB)

(73) Assignee: The University of Birmingham, Birmingham (GB)

( * ) Notice: Subject to any disclaimer, the term of this patent is extended or adjusted under 35 U.S.C. 154(b) by 65 days.

(21) Appl. No.: 14/130,254

(22) PCT Filed: Jun. 28, 2012

(86) PCT No.: PCT/GB2012/000555
§ 371 (c)(1),
(2), (4) Date: Mar. 13, 2014

(87) PCT Pub. No.: WO2013/004989
PCT Pub. Date: Jan. 10, 2013

(65) Prior Publication Data
US 2014/0212497 A1 Jul. 31, 2014

(30) Foreign Application Priority Data

Jul. 1, 2011 (GB) .................................. 1111516.9

(51) Int. Cl.
C07F 15/00 (2006.01)
B01J 2/00 (2006.01)
(52) U.S. Cl.
CPC ........... *C07F 15/0053* (2013.01); *B01J 2/006* (2013.01); *C07F 15/0033* (2013.01)
(58) Field of Classification Search
CPC .............................. A61K 49/00; A61K 51/12
See application file for complete search history.

(56) References Cited

U.S. PATENT DOCUMENTS 7,906,147 B2 * 3/2011 Hainfeld ............ A61K 49/0428
424/490
2010/0297019 A1 * 11/2010 Lanza ................ A61K 49/0002
424/9.2

FOREIGN PATENT DOCUMENTS

| CN | 101318979 A | 12/2008 |
| CN | 101458215 A | 6/2009 |
| CN | 101851502 A | 10/2010 |
| WO | 2005081721 A2 | 9/2005 |
| WO | 2006078816 A2 | 7/2006 |
| WO | 2009025475 A2 | 2/2009 |

OTHER PUBLICATIONS

P. Pramod et al. Photochemistry of Ruthenium Trisbipyridine Functionalized on Gold Nanoparticles (The Journal of Physical Chemistry Letters, 2006, 110, 20737-20741).*
Marie-Alexandra Neouze et al., Surface Modification and Functionalization of Metal and Metal Oxide Nanoparticles by Organic Ligands, Monatsh Chem, 139, 183-195, 2008.*
P. Pramod et al., Photochemistry of Ruthenium Trisbipyridine Functionalized on Gold Nanoparticles, The Journal of Physical Chemistry B , 1006, 110, 20737-20741.*
Jose M. Abad et al., Functionalization of Thioctic Acid-Capped Gold Nanoparticles for Specific Immobilization of Histidine-Tagged Proteins, JACS, 2005, 127, 5689-5694.*
Christophe Alric et al., Gadolinium Chelate Coated Gold Nanoparticles As Contrast Agents for Both X-rau Computed Tomography and Magnetic Resonance Imaging, J. Am. Chem. Soc, 2008, 130, 15678-15682.*
Pramod et al., "Photochemistry of ruthenium trisbipyridine functionalized gold nanoparticles", J, Phys. Chem. B, 2006, 110, 20737-2074.
Mayer et al., "Polypyridyl ruthenium complexes as coating agent for the formation of gold and silver nanocomposites in different media", New J. Chem., 2006, 30, 1628-1637.
Yu et al., "Synthesis and electrochemiluminescence of bis(2,2'-bipyridine)(5-amino-1,10-phenanthroline) ruthenium (II)-functionalized gold nanoparticles", J. Mater. Chem. 2011, 21, 12622-12625.
Elmes et al., "Luminescent ruthenium (II)-polypyridyl functionalized gold nanoparticles", J. Am. Chem. Soc., 2011, 133, 15862-15865.
A. L. Vavere et al., "A Novel Technology for the Imaging of Acidic Prostate Tumors by Positron Emission Tomography", Cancer Research, vol. 69, No. 10, May 15, 2009. pp. 4510-4516.
Deplanche Kevin et al., "Manufacture of Stable Palladium and Gold Nanoparticles on Native and Genetically Engineered Flagella Scaffolds", Biotechnology and Bioengineering, Wiley & Sons, Hoboken, NJ, vol. 101, No. 5, Dec. 1, 2008, pp. 873-880.
David J. Lewis et al., "Purely Heterometallic Lanthanide (III) Macrocycles through Controlled Assembly of Disulfide Bonds for Dual Color Emission", Journal of the American Chemical Society, vol. 133, No. 4, Feb. 4 2011, pp. 1033-1043.
A. Davies et al., "pH-controlled delivery of luminescent europium coated nanoparticles into platelets", Proceedings of the National Academy of Sciences, vol. 109, No. 6, Feb. 7, 2012, pp. 1862-1867.
British Search Report issued Feb. 20, 2012 in connection with related British Patent Appl. No. GB1111516.9.
PCT Search Report issued Sep. 10, 2012 in connection with related PCT/GB2012/000555.

\* cited by examiner

*Primary Examiner* — Michael G. Hartley
*Assistant Examiner* — Jagadishwar Samala
(74) *Attorney, Agent, or Firm* — Berliner & Associates (57) ABSTRACT The present invention relates to a method for preparing a composition comprising nanoparticles of a noble metal functionalized with at least one type of metal complex and surfactant. The method comprises providing a first solution comprising nanoparticles and surfactant, and a second solution comprising a first type of metal complex, and adding the second solution to the first solution. Each nanoparticle has a loading of at least 500 and the method permits independent control of particle size and loading and enables large particles with high loading to be reproduced without agglomeration.

16 Claims, 3 Drawing Sheets

COATED NANOPARTICLES

The present invention is concerned with the general field of metal particles with a coating providing additional functionality. In particular, it is concerned with coated nanoparticles.

Nanoparticles are defined as particles having a maximum diameter of between 1 and 500 nanometers. This particular size makes them of interest in a number of applications in the field of biotechnology, materials science and chemical engineering. In particular, nanoparticles are sufficiently large to permit the attachment of small molecules to provide additional functionality, whilst being sufficiently small to be incorporated in living organisms, or in small-scale process apparatus.

The use of nanoparticles functionalised with luminescent probes is known. For example, the present inventor has previously published the results of work involving the functionalisation of gold and platinum nanoparticles with lanthanide photoluminescent probes. These probes allow visualisation of the location of the particles following irradiation with UV light. Thus, for example, it is possible to track movement of the particles within fluid flows, such as in nanoscale lab-on-a chip type devices, or within biological systems. However, the efficiency of lanthanide-based probes is relatively low; thus, it can be difficult to detect low concentrations of the nanoparticles.

It is also possible to use luminescent probes based on small organic molecules. For example, in the field of biotechnology, it is known to functionalise biomolecules (such as peptides and proteins) with fluorescent marker groups in order to track uptake of those biomolecules into cells. Such organic markers frequently have high efficiency in terms of light absorbance and emission, and can be activated by visible light. Again, however, there are a number of difficulties which arise. One problem with this approach is that chemical derivatization of the biomolecule is generally required in order to attach the marker group. Whilst this may be possible for a single marker, it becomes increasingly difficult to attach more than one marker with reasonable yield.

A second problem with the use of organic-based chromophores is their tendency to bleach under continued exposure to light, thereby reducing the effectiveness of the marker over time.

The use of nanoparticles functionalised with transition metal-based chromophores (such as ruthenium, iridium, osmium, zinc metal complexes) has the potential to address both of these issues. Functionalisation of nanoparticles through reversible surface binding is known, such as the attachment of sulfur-based groups to the surface of a gold particle. In this way, several different chromophores can be attached together onto an individual particle, without the need for a complex synthetic process. Furthermore, transition metal-based chromophores are able to provide long-lived luminescence without the risk of bleaching.

According to a first aspect of the present invention there is provided a composition comprising nanoparticles of a noble metal functionalised with at least one type of metal complex and surfactant, wherein each nanoparticle has a loading of at least 500.

As used herein "loading" is defined as the total number of complex molecules with which each nanoparticle is functionalised.

The nanoparticles may be from 3 to 500 nm, from 10 to 400 nm, from 40 to 300 nm or from 50 to 150 nm for example 5, 15, 25, 50 or 100 nm. The inventors have found that that agglomeration is more likely to occur at increasing concentration, particularly when the complexes are charged.

The loading is to some extent dependent on the size of the particle. For particles smaller than 30 nm, the loading may be at least 1000, at least 2000 or even at least 4000. For particles larger than 30 nm but smaller than 60 nm, the loading may be at least 7000, at least 10,000, at least 20,000 or even at least 30,000. For particles larger than 60 nm, the loading may be at least 40,000, at least 60,000, at least 80,000 or even at least 100,000.

In certain embodiments the complex is a charged complex.

In certain embodiments, the composition is a solution. The solution may have a concentration of unagglomerated functionalised nanoparticles of at least 0.2 nM, at least 1 nM, at least 3 nm or at least 6 nM.

The metal complex may be any complex suitable for imaging and/or therapy. Suitable complexes for imaging include luminescent (e.g. chemoluminescent, eletroluminescent or fluorescent), radioactive or MRI active complexes. Suitable complexes for therapy include complexes having anti-cancer activity.

The metal complexes may be selected from complexes of any transition (i.e. d-block), p-block or rare earth metal. Examples include boron, ruthenium, iridium, osmium, zinc and gadolinium.

Ruthenium complexes are particularly attractive for use in biological applications because they can be excited with visible light, emit visible (red) light, have a large Stokes shift and are biocompatible.

As used herein, noble metal has its usual meaning to refer to the elements in Groups 10 and 11 of the periodic table of elements. In some further embodiments, the noble metal is selected from palladium, silver, platinum and gold. In some still further embodiments, the noble metal is selected from platinum and gold. In some still further embodiments, the noble metal is gold.

It will be understood that photoluminescence is commonly encountered in transition metal complexes with ligands having low lying π* orbitals, such as aromatic ligands and particularly heteroaromatic ligands. In some embodiments, the metal complex comprises at least one ligand selected from a diimine (such as bipyridine or phenanthroline). In some further embodiments, the metal complex comprises between one and three ligands independently selected from bipyridines and phenanthrolines. In some still further embodiments, the metal complex comprises three ligands independently selected from bipyridines and phenanthrolines.

The bipyridines and/or phenanthrolines may be functionalised or unfunctionalised. Thus, in some embodiments, the metal complex comprises three ligands independently selected from those of formula (I) and (II):

-continued (II)

where n=0, 1, 2, 3, or 4; p=0, 1, 2, or 3; and q=0, 1, or 2; and each R is selected from $C_1$-$C_{10}$ alkyl (including cycloalkanyl), $C_2$-$C_{10}$ alkenyl, or $C_2$-$C_{10}$ alkynyl, optionally substituted with up to 3 groups selected from amino, hydroxyl, $C_1$-$C_4$ ether, thiol, $C_1$-$C_4$ thioether, nitro, nitrile, carboxylate, $C_1$-$C_4$ ester, phenyl, pyridinyl, pyrimidinyl, furanyl, pyrrolyl, thiophenyl, imidazolyl, and thiazolyl; provided that the complex comprises at least one ligand having at least one thiol group.

Without wishing to be bound by theory, it is believed that the presence of the thiol group allows the complex to bind to the surface of the metal nanoparticle.

In some embodiments, the complex comprises at least one ligand having at least two thiol groups. In some embodiments, the complex comprises at least one ligand having at least one primary thiol group. In some further embodiments, the complex comprises at least one ligand having at least two primary thiol groups. In some still further embodiments, the complex comprises at least one ligand of structure (III):

(III)

In some further embodiments, the complex has the structure (IV):

(IV)

Other suitable complexes include GdSH:

The composition may comprise nanoparticles functionalised with more than type of metal complex. It will be understood that the types of metal complex may be chosen to allow multimodal imaging (e.g. detection of luminescence at different wavelengths, luminescent and MRI imaging, or combined imaging and therapy).

The inventor has surprisingly found that functionalised nanoparticles, particularly large nanoparticles and/or nanoparticles with a high loading and/or nanoparticles functionalised with charged complexes, have a tendency to agglomerate, and that the inclusion of a surfactant helps prevent such agglomeration. "Surfactant" is used in the usual sense of an amphiphilic molecule having a water soluble part and a water insoluble part. Suitable surfactants include peptides and proteins, amphipathic polymers, and polyethers.

In some embodiments, the surfactant is a polyether. An exemplary polyether surfactant is polyoxyethylene (20) sorbitan monolaurate, known as polysorbate 20 and under the brand name TWEEN 20®. In some still further embodiments, the surfactant is a fluorinated polyether. An exemplary fluorinated polyether is available from DuPont Specialty Chemicals under the brand name ZONYL 7950®. The present inventor has surprisingly found that use of a fluorinated polyether surfactant allows an even higher concentration of functionalised nanoparticles to be produced without agglomeration.

According to the second aspect of the invention, there is provided a method for preparing a composition according to the first aspect of the invention, comprising providing a first solution comprising nanoparticles and surfactant, and a second solution comprising a metal complex, and adding the second solution to the first solution.

The method of the present invention allows the size of the nanoparticles to be chosen independently of the nature/loading of the metal complex. This is not possible in other processes such as ones where the nanoparticles are produced in situ from a noble metal salt and reducing agent in the presence of a coating agent.

In some embodiments, adding the second solution to the first solution comprises titrating the second solution into the first solution whilst measuring the UV-Vis absorption spectrum.

Additional solutions (e.g. a third or a third and fourth) containing different metal complexes may be added to the first and second solutions. It will be understood that the result of adding different metal complex solutions is nanoparticles functionalised with two, three or more different metal complexes.

The nanoparticle compositions of the present invention may be useful for imaging of living cells, for example to determine which cells have internalised the nanoparticles.

Thus, according to a third aspect of the invention there is provided the use of a composition according to the first aspect of the invention for cell imaging.

The nanoparticle compositions of the present invention may be useful for marking biomolecules, for example to determine whether those biomolecules are taken up by living cells. The cells labelled with nanoparticles can also be introduced for imaging blood flow and tracking cell migration. Thus, according to a fourth aspect of the invention there is provided the use of a composition according to the first aspect of the invention for marking biomolecules and/or incorporating the nanoparticles into cells. Suitable biomolecules include peptides, proteins and nucleic acids.

Embodiments of the invention will be described by way of example only with reference to the accompanying drawings in which.

A. METAL COMPLEX PREPARATION

2,2'-Bipyridinyl-4,4'-diol: 4,4'-BpyOH[1]

To a solution of 4,4'-dimethoxy-2,2'-bipyridine (3.055 g, 14.13 mmol) in 180 ml of glacial acetic acid was added 48 wt % HBr solution in water (25 ml, 146 mmol). The mixture was refluxed overnight at 140° C. under $N_2$ (g). The mixture was allowed to cool and the solvent was removed in vacuo to render a white solid. The residue was dissolved in 100 ml of water and neutralised by adding aqueous ammonium hydroxide. The white solid (2.425 g, 12.89 mmol, 91% yield) was filtered and dried, and used in the next step without further purification.

$^1$H NMR (300 MHz, NaOD/$D_2O$): $\delta_H$=7.74 (s, 1H, OH), 7.38 (d, 2H, $^3J_{H5}$=5.9 Hz, $H_6$), 6.34 (d, 2H, $^4J_{H5}$=2.4 Hz, $H_3$), 5.85 (dd, 2H, $^3J_{H6}$=5.9 Hz, $^4J_{H3}$=2.4 Hz, $H_5$). EI-MS (+): m/z 188.1 [M]$^+$·, 160.1 [M–$N_2$]$^+$·, 94.0 [c-$C_5H_3N$—OH]$^+$· IR (cm$^{-1}$): 3209.17, 3059.21, 2760.30, 1594.48, 1523.34, 1475.20, 1393.46, 1218.35.

4,4'-bis(hex-5-en-1-yloxy)-2,2'-bipyridine: 4,4'-Bpy-Hex[2]

4,4'-dihydroxybipyridine (1.1006 g, 5.85 mmol) and NaH (2.40 g, 60.03 mmol, 60% in mineral oil) were dissolved in 70 ml of dry DMF (dried over 3 Å molecular sieves under $N_2$ (g) for 1 hr) and the white suspension was stirred at 60° C. under nitrogen for 1 hr. 6-bromohex-1-ene (4.1 g, 25.1 mmol) was added dropwise, and the reaction mixture was heated at 60° C. for 20 hr to render a pale yellow/brown solution. The reaction was cooled to room temperature and the NaH was quenched by adding 75 ml of ice-cooled ethanol. The solvent was removed in vacuo to give a pale brown residue. The residue was extracted with DCM/water, and the organic layer was dried over MgSO4. The DCM was removed in vacuo and the crude was purified by recrystallisation from ethanol to yield 4,4'-BpyHex (1.100 g, 3.12 mmol, 53% yield) as a crystalline white solid.

$^1$H NMR (400 MHz, CDCl$_3$): $\delta_H$=8.45 (d, 2H, $^3J_{H5}$=5.7 Hz, $H_6$), 7.94 (d, 2H, $^4J_{H5}$=2.5 Hz, $H_3$), 6.82 (dd, 2H, $^3J_{H6}$=5.7 Hz, $^4J_{H3}$=2.6 Hz, $H_5$), 5.83 (m, 2H, $^3J_{H12}$=17.1 Hz, $^3J_{H13}$=10.3 Hz, $^3J_{H10}$=6.6 Hz, $H_{11}$), 5.04 (m, 2H, $^2J_{11}$=17.1 Hz, $^2J_{13}$=2.0 Hz, $^4J_{H10}$=1.5 Hz, $H_{12}$), 4.98 (m, 2H, $^3J_{H11}$=10.3 Hz, $^2J_{H12}$=2.0 Hz, $^4J_{H10}$=1.3 Hz, $H_{13}$), 4.14 (t, 4H, $^3J_{H5}$=6.5 Hz, $H_7$), 2.14 (m, 4H, $H_{10}$), 1.84 (m, 4H, $H_8$) 1.59 (m, 4H, $H_9$).

$^{13}$C NMR (400 MHz, CDCl$_3$): $\delta_C$=166.1 ($C_2$), 157.9 ($C_4$), 150.1 ($C_6$), 138.3 ($C_{11}$), 114.9 ($C_{12}$), 111.3 ($C_5$), 106.7 ($C_3$), 67.8 ($C_7$), 33.3 ($C_{10}$), 28.4 (Ca), 25.2 ($C_9$).

TOF ES-MS(+): m/z 375.2 [M+Na]$^+$·, 353.2 [M+H]$^+$·.

IR (cm$^{-1}$): 2951.89, 2920.38, 1576.56, 1558.36, 1456.46, 1296.78, 1244.82, 1003.27.

Ruthenium (II) bis-bipyridine Chloride: [Ru(bpy)$_2$Cl$_2$]·2H$_2$O[3]

200 ml of 2-methoxyethanol was purged with nitrogen for 15 min and Ru(COD)Cl$_2$ (dichloro(1,5-cyclooctadiene)ruthenium (II) polymer) (501.0 mg, 1.79 mmol) and LiCl (593.5 mg, 14.0 mmol) were added. The suspension was stirred at reflux for 30 min under nitrogen. 2,2'-bipyridine (547.8 mg, 3.51 mmol, 1.96 eq) was dissolved in 2-methoxyethanol (50 ml) and added dropwise to the refluxing mixture, over 15 min. The solution was left to reflux overnight to give a dark purple solution. This was cooled to room temperature under nitrogen, and the solvent was removed in vacuo to render a dark oil. This oil was added to cold, fast-stirring acetone (100 ml) in an ice-bath and left to stir for 1 hr, and then placed in the fridge overnight to precipitate. The black solid was filtered, and washed with water and diethyl ether to give [Ru(bpy)$_2$Cl$_2$]·2H$_2$O (385.8 mg, 0.741 mmol, 41% yield) as a dark green microcrystalline solid.

$^1$H NMR (300 MHz, DMSO): $\delta_H$=9.97 (d, 2H, $^3J_{H5}$=4.7 Hz, H$_6$), 8.64/8.49 (d, 2H, $^3J_{H4/H4'}$=7.8 Hz, H$_3$/H$_{3'}$), 8.07 (m, 2H, H$_4$), 7.77 (m, 2H, H$_5$), 7.68 (m, 2H, H$_{4'}$), 7.51 (d, 2H, $^3J_{H5'}$=4.6 Hz, H$_{6'}$), 7.10 (m, 2H, H$_{5'}$).

$^{13}$C NMR (400 MHz, DMSO): $\delta_C$=160.1/158.1 (C$_2$/C$_{2'}$), 153.1 (C$_6$), 151.9 (C$_{6'}$), 134.5 (C$_4$), 133.2 (C$_{4'}$), 125.3/125.2 (C$_5$/C$_{5'}$), 122.8/122.4 (C$_3$/C$_{3'}$).

TOF ES-MS(+): m/z 523.0 [M+K]$^+$·, 507.0 [M+Na]$^+$, 481.1 [Ru(bpy)2(OMe)Cl+H]$^+$·, 449.0 [M−Cl]$^+$·.

TOF LD-MS(+): m/z 484.2 [M]$^+$·, 449.4 [M−Cl]$^+$·, 413.5 [M−2Cl]$^+$·, 328.7 [M−bpy]$^+$·, 293.2 [Ru(bpy)Cl]$^+$·.

UV-VIS (DCM) $\lambda_{max}$/nm: 555, 378, 300.

IR (cm$^{-1}$): 3100.21, 3068.88, 3029.23, 1612.67, 1600.61, 1459.69, 1442.19, 1417.57, 1307.90, 1264.82.

[Ru(bpy)$_2$(4,4'-BpyHex)](PF$_6$)$_2$[2]

[Ru(bpy)₂Cl₂]·2H₂O (107.7 mg, 0.207 mmol) and 4,4'-BpyHex (119.1 mg, 0.338 mmol) were heated to reflux in ethanol (10 ml) for 17 hr under nitrogen to give a deep red solution. This was allowed to cool to room temperature and was concentrated to 3 ml in vacuo. A saturated solution of NH₄PF₆ (3.5 ml) was added, followed by 7 ml of H₂O, and a red precipitate was formed. The flask was put in the fridge for 30 min, and the red solid was filtered under suction, washed with water and ether to yield [Ru(bpy)₂(4,4'-Bpy-Hex)](PF₆)₂ (131.6 mg, 0.125 mmol, 60.2% yield) as a red solid.

$^1$H NMR (400 MHz, CD$_3$CN): $\delta_H$=8.47 (dd, 4H, $^3J_{H4'1/H4''}$=8.3 Hz, $^3J_{H5'/H5''}$=4.5 Hz, H$_3$/H$_{3''}$), 8.06-7.99 (m, 4H, H$_{4'}$/H$_{4''}$), 7.97 (d, 2H, $^4J_{H5}$=2.5 Hz, H$_3$), 7.81/7.71 (2×(d, 2H, $^3J_{H5'/H5''}$=5.5 Hz), H$_{6'}$/H$_{6''}$), 7.43-7.39/7.38-7.33 (2×m) 4H, H$_5$/H$_{5''}$), 7.41 (d, 2H, $^3J_{H5}$=6.5 Hz, H$_6$), 6.90 (dd, 2H, $^3J_{H6}$=6.5 Hz, $^4J_{H3}$=2.5 Hz, H$_5$), 5.86 (m, 2H, $^3J_{H12}$=17.1 Hz, $^3J_{H13}$=10.3 Hz, $^3J_{H10}$=6.6 Hz, H$_{11}$), 5.05 (m, 2H, $^3J_{H11}$=17.1 Hz, H$_{12}$), 4.97 (m, 2H, $^3J11$=10.3 Hz, H$_{13}$), 4.19 (t, 4H, $^3J_{H8}$=6.5 Hz, H$_7$), 2.17-2.09 (m, 4H, H$_{10}$), 1.85-1.77 (m, 4H, H8), 1.61-1.51 (m, 4H, H$_9$).

$^{13}$C NMR (400 MHz, CD$_3$CN): $\delta_C$=153.0 (C$_6$), 152.7/152.5 (C$_{6'}$/C$_{6''}$), 139.5 (C$_{11}$), 138.3 (C$_{4'}$/C$_{4''}$), 128.3 (C$_{5'}$/C$_{5''}$), 125.0 (C$_{3'}$/C$_{3''}$), 115.3 (C$_{12}$), 115.0 (C$_5$), 112.3 (C$_3$), 70.5 (C$_7$), 33.8 (C$_{10}$), 28.7 (C$_8$), 25.7 (C$_9$).

TOF ES-MS(+): m/z 911.1 [M−PF6]$^+$, 383.2 [M−2PF6]$^{2+}$
TOF LD-MS(+): m/z 911.2 [M−PF6]$^+$.
UV-VIS (MeCN) $\lambda_{max}$/nm: 461, 436 (sh), 288, 227.
Emission (MeCN, $\lambda_{exc}$=460 nm) $\lambda_{max}$/nm: 645.
IR (cm$^{-1}$): 2934.88, 2866.90, 1611.91, 1490.73, 1464.92, 1445.33, 1337.03, 1313.51, 1219.38.

[RU($^3$PY)2(BPYSAC)](PF$_6$)$_2$$^2$

A solution of thioacetic acid (100 mg, 1.31 mmol) and ABCN (1,1'-azobiscyclohexane carbonitrile) (120 mg, 0.49 mmol) in dry THF (2 ml) was heated at 60° C. and degassed under nitrogen for 30 min. [Ru(bpy)$_2$(4,4'-bpyHex)](PF$_6$)$_2$ (105.9 mg, 0.100 mmol) was dissolved in 4 ml THF, and added dropwise to the solution. The double bond disappearance was monitored by proton NMR. The reaction was stirred at 60° C. followed by addition of one portion of ABCN (120 mg, 0.49 mmol) and thioacetic acid (100 mg, 1.31 mmol) after 15 hr, and another portion of ABCN (120 mg, 0.49 mmol) and thioacetic acid (100 mg, 1.31 mmol) after 24 hr. After a total of 40 hr stirring the reaction was pushed to completion and the ABCN was quenched with saturated NaHCO$_3$ solution. (10 ml). The THF was removed in vacuo, and the residue was extracted in DCM/water, washed with brine, and dried over MgSO$_4$. The DCM was removed in vacuo and the solid was filtered under suction, and washed with a copious amount of hexane and diethyl ether to yield [Ru(bpy)$_2$(BpySAc)] (PF$_6$)$_2$ (52.9 mg, 0.044 mmol, 43.8% yield) as a red solid.

$^1$H NMR (400 MHz, CD$_3$CN): δ$_H$=8.47 (dd, 4H, $^3$J$_{H4'/H4''}$=8.1 Hz, $^4$J$_{H5'H5''}$=4.6 Hz, H$_3$/H$_{3''}$), 8.03 (m, 4H, H$_4$/H$_{4''}$), 7.97 (d, 2H, $^4$J$_{H5}$=2.5 Hz, H$_3$), 7.81/7.71 (2×(d, 2H, $^3$J$_{H5'/H5''}$=5.5 Hz), H$_6$/H$_{6''}$), 7.43-7.39/7.37-7.33 ((2×m), 4H, H$_5$/H$_{5''}$), 7.41 (d, 2H, $^3$J$_{H5}$=6.5 Hz, H$_6$), 6.90 (dd, 2H, $^3$J$_{H6}$=6.5 Hz, $^4$J$_{H3}$=2.5 Hz, H$_5$), 4.18 (t, 4H, $^3$J$_{H8}$=6.5 Hz, H$_7$), 2.85 (t, 4H, $^3$J$_{H11}$=7.3 Hz, H$_{12}$), 2.27 (s, 6H, H$_{14}$), 1.84-1.76 (m, 4H, H$_8$), 1.61-1.53 (m, 4H, H$_{11}$), 1.52-1.38 (m, 8H, H$_9$/H$_{10}$).

$^{13}$C NMR (400 MHz, CDCl$_3$): δ$_C$=153.0 (C$_6$), 152.7/152.5 (C$_6$/C$_{6''}$), 138.3 (C$_4$/C$_{4''}$), 128.5 (C$_5$/C$_{5''}$), 125.1 (C$_3$/C$_{3''}$), 115.1 (C$_5$), 112.3 (C$_3$), 70.6 (C$_7$), 30.8 (C$_{14}$), 30.2 (C$_{11}$), 29.4 (C$_{12}$), 29.1 (C$_9$), 28.9/25.8 (C$_9$/C$_{10}$).

TOF ES-MS(+): m/z 1063.2 [M−PF$_6$]$^+$, 459.1 [M−2PF$_6$]$^{2+}$.

UV-VIS (MeCN) λ$_{max}$ in nm: 462 (log ε=4.08), 436 (sh), 289 (log ε=4.79), 228.

Emission (MeCN) λ$_{max}$ in nm: 645.

IR (cm$^{-1}$): 2930.48, 2857.01, 1682.59 (C=O), 1610.90, 1556.48, 1491.59, 1464.36, 1444.15, 1396.26, 1339.30, 1277.61, 1221.99, 1119.75 (C(O)—C).

Anal. Calc. for C$_{46}$H$_{52}$F$_{12}$N$_6$O$_4$P$_2$RuS$_2$: C, 45.73; H, 4.34; N, 6.96. Found: C, 45.66; H, 4.17; N, 7.03.

RuBpySH

NH$_4$OH (aq) solution (50 μl, 30% wt) was added to RuBpySAc (100 μl, 1.52 mM in MeCN, 152 nmol) and shaken for ten min in a sealed vial to give RuBpySH, directly prior to titration into the colloid. TOF LD-MS(+): m/z 829.7 (M−2PF$_6$H$^+$.

[Ir(ppy)$_2$(μ-Cl)]$_2$

The method was modified from Sprouse et al.[4]

A solution of Iridium trichloride hydrate (805 mg, 2.70 mmol) and 2-phenylpyridine (1.593 g, 10.3 mmol) in 2-methoxyethanol (60 mL) was refluxed at 130° C. overnight to give a yellow/brown suspension. This was left to cool and was filtered under suction to render a yellow powder. The residue was washed with ethanol (100 mL) and dissolved in DCM (150 mL). The solution was filtered and hexane (20 mL) and toluene (50 mL) was added. The volume was reduced in vacuo to 100 mL and cooled on ice to crystallise. The product was retrieved by filtration as yellow crystalline solid (0.7369 g, 0.687 mmol, 51% yield). R$_f$=0.81 (DCM:methanol 10:1).

$^1$H NMR (300 MHz, d$^6$-DMSO): δ$_H$=9.81/9.53 (d, 4H, $^3$J$_{Hb/Hb'}$=5.8 Hz, H$_a$/H$_{a'}$), 8.27/8.19 (d, 4H, $^3$J$_{Hc/Hc'}$=7.9 Hz, H$_d$/H$_{d'}$), 8.10/8.01 (m (dd), 4H, H$_c$/H$_{c'}$), 7.79/7.74 (d, 4H, $^3$J$_{Hg/Hg'}$=7.9 Hz, H$_h$/H$_{h'}$), 7.57/7.46 (m (dd), 4H, H$_b$/H$_{b'}$), 6.79 (m, 8H, H$_f$/H$_{f'}$, H$_g$/H$_{g'}$), 6.25/5.66 (dd, 4H, $^3$J$_{Hf/Hf'}$=7.3 Hz, H$_e$/H$_{e'}$). $^{13}$C NMR (400 MHz, d$^6$-DMSO): δ$_C$=166.9/152.0/145.4/143.7/143.1 (quaternary C), 152.1/150.6 (C$_a$/C$_{a'}$), 139.2/138.1 (C$_c$/C$_{c'}$), 131.2/129.6 (C$_e$/C$_{e'}$), 129.9/128.9/122.2/121.9 (C$_f$/C$_{f'}$/C$_g$/C$_{g'}$), 124.8/123.8 (C$_h$/C$_{h'}$), 123.5/122.8 (C$_b$/C$_{b'}$), 120.0/119.4 (C$_d$/C$_{d'}$). TOF ES-MS(+): m/z 1037 [M−Cl]$^+$, 999 [Ir$_2$(ppy)$_4$]$^+$, 543 [Ir(ppy)$_2$+K]$^+$, 501 [Ir(ppy)$_2$]$^+$. UV-VIS (MeCN) λ$_{max}$ [nm]=259. Emission (MeCN, λ$_{exc}$=355 nm) λ$_{max}$ [nm]=508 nm.

IR [cm$^{-1}$]: 3039.71, 1950.08, 1604.75, 1581.01, 1561.02, 1476.18, 1414.17, 1029.64, 753.66.

[Ir(ppy)₂(BpyHex)]Cl: IrBpyHex

[Ir(ppy)₂(μ-Cl)]₂ (401.9 mg, 0.375 mmol) and BpyHex (203.0 mg, 0.573 mmol) were dissolved in CH₂Cl₂/MeOH (45 mL, 2:1) and refluxed overnight at 60° C. under nitrogen. The solvent was removed in vacuo to render yellow crystals. The residue was purified by chromatography (flash silica column, DCM:methanol 10:1). The eluent was removed in vacuo, the product was cooled to crystallise, then recrystallised in acetone to yield a yellow powder. The product (0.2485 g, 0.280 mmol, 75% yield) was washed with diethyl ether and filtered. $R_f$=0.44 (DCM:methanol 10:1).

$^1$H NMR (400 MHz, d$^6$-DMSO): $\delta_H$=8.46 (s, 2H, H$_3$), 8.25 (d, 2H, $^3J_{Hb}$=8.2 Hz, H$_a$), 7.93 (m, 4H, H$_b$/H$_h$), 7.69 (d, 2H, $^3J_{Hc}$=5.6 Hz, H$_d$), 7.59 (d, 2H, $^3J_{H5}$=6.6 Hz, H$_6$), 7.28 (dd, 2H, $^3J_6$=6.6 Hz, $^4J_{H3}$=2.5 Hz, H$_5$), 7.19 (t, 2H, $^3J_{Hb}$=$^3J_{Hd}$=5.7 Hz, H$_c$), 7.00 (t, 2H, $^3J_{Hf}$=$^3J_{Hh}$=7.5 Hz, H$_g$), 6.88 (t, 2H, $^3J_{He}$=$^3J_{Hg}$=7.5 Hz, H$_f$), 6.19 (d, 2H, $^3J_{Hf}$=7.5 Hz, H$_e$), 5.82 (m, 1H, H$_{11}$), 5.01 (m, 2H, H$_{13}$/H$_{14}$), 4.24 (d, 4H, $^3J_{H8}$=6.3 Hz, H$_7$), 2.10 (q, 4H, $^3J_{H9}$=$^3J_{H11}$=7.0 Hz, H$_{10}$), 1.78 (qu, 4H, $^3J_{H7}$=$^3J_9$=6.9 Hz, H$_8$), 1.53 (m, 4H, H$_9$). $^{13}$C NMR (400 MHz, d$^6$-DMSO): $\delta_C$=150.5 (C$_6$), 148.7 (C$_d$), 138.5/138.3 (C$_b$/C$_{11}$), 131.1 (C$_e$), 1130.1 (C$_f$), 125.9 (C$_h$), 125.0 (C$_c$), 123.8 (C$_g$), 121.9 (C$_a$), 115.1 (C$_{12}$), 114.5 (C$_5$), 111.9 (C$_3$), 69.1 (C$_7$), 32.6 (C$_{10}$), 27.6 (C$_8$), 24.5 (C$_9$). TOF ES-MS(+): m/z 853.5 [M]$^+$ UV-VIS (MeCN) $\lambda_{max}$ [nm]= 255, 227. Emission (MeCN, $\lambda_{exc}$=355 nm) $\lambda_{max}$ [nm]=588 nm. IR [cm$^{-1}$]: 3044.54, 2939.79, 1605.57, 1472.23, 1436.20, 1340.50, 1283.71, 1225.59, 1030.66, 994.33, 756.42.

[Ir(ppy)₂(BPySAc)]Cl: IrBpySAc

Thioacetic acid (188 mL, 2.630 mmol) and ABCN (1,1'-azobiscyclohexane carbonitrile) (252 mg, 1.031 mmol) in dry THF (4 mL) were heated at 60° C. and degassed under $N_2$ (g) for 30 min. [Ir(ppy)₂(BpyHex)]Cl (204.1 mg, 0.230 mmol) in dry THF (10 mL) was added dropwise and the mixture was stirred at 60° C. under $N_2$ (g). The progress of the reaction was monitored by the disappearance of the double bond by ¹H NMR. Thioacetic acid (100 mL, 1.399 mmol) and ABCN (125 mg, 0.512 mmol) were added after 18 hrs, another portion of thioacetic acid (120 mL, 1.679 mmol) and ABCN (150 mg, 0.614 mmol) was added after 22 hrs. After a total of 45 hrs, the reaction was pushed to completion and the ABCN was quenched with saturated aqueous NaHCO₃(aq) solution (150 mL). The solution was extracted with DCM/H₂O and the organic layer was dried over MgSO₄ and filtered. The solvent was removed in vacuo to render a dark brown viscous residue. This was sonicated in hexane (200 mL) and stirred for 48 hr. The residue was purified by chromatography (flash silica column, DCM:methanol 10:1). The eluent was removed in vacuo to yield a bright yellow solid. The product (42 mg, 40.4 μmol, 18% yield) was washed with ether and dried. ¹H NMR (400 MHz, d⁶-DMSO): $\delta_H$=8.44 (d, 2H, $^4J_{H5}$=2.5 Hz, H₃), 8.25 (d, 2H, $^3J_{Hb}$=8.1 Hz, H$_a$), 7.92 (m, 4H, H$_b$/H$_h$), 7.68 (d, 2H, $^3J_{Hc}$=5.1 Hz, H$_d$), 7.58 (d, 2H, $^3J_{45}$=6.4 Hz, H₆), 7.27 (dd, 2H, $^3J_{H6}$=6.4 Hz, $^4J_{H3}$=2.4 Hz, H₅), 7.18 (m (dd), 2H, H$_c$), 6.99 (dt, 2H, $^3J_{HfHh}$=7.5 Hz, $^4J_{He}$=1.0 Hz, H₉), 6.878 (dt, 2H, $^3J_{He/Hg}$=7.4 Hz, $^4J_{Hh}$=1.1 Hz, H$_f$), 6.18 (d, 2H, $^3J_{Hf}$=6.6

Hz, $H_e$), 4.21 (t, 4H, $^3J_{H8}$=6.1 Hz, $H_7$), 2.83 (t, 4H, $^3J_{H11}$=7.2 Hz, $H_{12}$), 2.30 (s, 4H, $H_{14}$), 1.75 (m, 4H, $H_{10}$), 1.52 (m, 4H, $H_8$), 1.40 (m, 8H, $H_3/H_{11}$). $^{13}$C NMR (400 MHz, d$^6$-DMSO): $\delta_C$=177.2/169.9/156.9/143.9 (quaternary C), 150.5 ($C_6$), 148.7 ($C_d$), 138.5/125.0 ($C_b/C_h$), 131.1 ($C_e$), 130.1 ($C_f$), 123.8 ($C_c$), 121.9 ($C_g$), 119.9 ($C_a$), 114.5 ($C_5$), 111.9 ($C_3$), 69.2 ($C_7$), 30.6 ($C_{14}$), 29.0 ($C_8$), 28.2 ($C_{12}$), 27.7 ($C_{10}$), 26.5/24.8 ($C_9/C_{11}$). TOF MALDI-MS(+): m/z 1064.20 [M+Na]$^+$, 1006.19 [M−Cl]$^+$ HRMS (ES$^+$): Calc. for $C_{48}H_{52}IrN_4O_4S_2$ 1005.3060, found 1005.3046 Anal. calc. for $C_{48}H_{82}ClIrN_4O_4S_2$: C, 55.4; H, 5.0; N, 5.4. Found: C, 55.1; H, 4.9; N, 5.2. UV-VIS (MeCN) $\lambda_{max}$ [nm]=255, 228. UV-VIS (1% MeCN/H$_2$O) $\lambda_{max}$ [nm]=255, 228. Emission (MeCN, $\lambda_{exc}$=355 nm) $\lambda_{max}$ [nm]=584 nm. Emission (1% MeCN/H$_2$O, $\lambda_{exc}$=355 nm) $\lambda_{max}$ [nm]=572 nm. IR [cm$^{-1}$]: 2925.48, 1681.50, 1604.99, 1476.13, 1417.16, 1337.29, 1268.83, 1224.88, 1062.79, 1029.71, 951.81, 756.51.

[Ir(ppy)$_2$(BpySH)]Cl: IrBpySH (Yellow)

To [Ir(ppy)$_2$(BpySAc)]Cl (50 μL, 7.96 mM in MeCN, 398 nmol) was added NH$_4$OH$_{(aq)}$ solution (50 μL, 30% wt). The mixture was shaken for ten min in a sealed vial to render [Ir(ppy)$_2$(BpySH)]Cl, directly prior to titration into the colloid TOF MALDI-MS(+): 920.15 [M−Cl]$^+$ UV-VIS (MeCN) $\lambda_{max}$ [nm]=255, 227.

[Ir(ppy)$_2$(PhenHex)]PF$_6$: IrPhenHex

[Ir(ppy)$_2$(μ-Cl)]$_2$ (290 mg, 0.250 mmol) and PhenHex (177 mg, 0.499 mmol) were dissolved in CH$_2$Cl$_2$/MeOH (45 mL, 2:1) and refluxed overnight at 60° C. under nitrogen. NH$_4$PF$_6$ (600 mg) was added to the cooled reaction, and this was stirred for 30 min. The solvent was removed in vacuo and the resulting solid was extracted in DCM/water. The residue was purified by chromatography (flash silica column, DCM:methanol 20:1) to yield an orange powder. The product (0.291 g, 0.285 mmol, 53% yield) was washed with diethyl ether and filtered. R$_f$=0.36 (DCM:methanol 10:1).

[Ir(ppy)$_2$(PhenSAc)]Cl: IrPhenSAc

Thioacetic acid (188 mL, 2.630 mmol) and ABCN (1,1'-azobiscyclohexane carbonitrile)

(252 mg, 1.031 mmol) in dry THF (4 mL) were heated at 60° C. and degassed under $N_2$ (g) for 30 min. [Ir(ppy)$_2$(BpyHex)]Cl (197 mg, 0.193 mmol) in dry THF (10 mL) was added dropwise and the mixture was stirred at 60° C. under $N_2$(g). The progress of the reaction was monitored by the disappearance of the double bond by $^1$H NMR. Thioacetic acid (100 mL, 1.399 mmol) and ABCN (125 mg, 0.512 mmol) were added after 18 hrs, another portion of thioacetic acid (120 mL, 1.679 mmol) and ABCN (150 mg, 0.614 mmol) was added after 22 hrs. After a total of 45 hrs, the reaction was pushed to completion and the ABCN was quenched with saturated aqueous NaHCO$_3$(aq) solution (150 mL). The solution was extracted with DCM/H$_2$O and the organic layer was dried over MgSO$_4$ and filtered. The solvent was removed in vacuo to render an orange solid, which was stirred in hexane (40 mL) for 4 hr, and then filtered and washed with hexane (3×10 mL) to give the product (55 mg, 0.051 mmol, 24% yield) as an orange powder.

$^1$H NMR (400 MHz, d$^6$-DMSO): $\delta_H$=8.36 (s, 2H, H$_3$), 8.25 (d, 2H, $^3J_{Hb}$=8.0 Hz, H$_a$), 7.93 (m, 4H, H$_b$/H$_1$), 7.87 (dd, 2H, $^3J_{Ha/c}$=7.8 Hz, H$_b$), 7.56 (m, 4H, H$_d$/H$_2$), 7.03 (m, 4H, H$_g$/H$_c$), 6.93 (m (dt), 2H, H$_f$), 6.31 (d, 2H, $^3J_{Hf}$=7.5 Hz, H$_e$), 4.35 (t, 4H, $^3J_{H8}$=6.1 Hz, H$_7$), 2.86 (t, 4H, $^3J_{H11}$=7.3 Hz, H$_{12}$), 2.30 (s, 4H, H$_{14}$), 1.89 (m, 4H, H$_8$), 1.55 (m, 8H, H$_9$/H$_{10}$), 1.44 (m, 4H, H$_{11}$). $^{13}$C NMR (400 MHz, d$^6$-DMSO): $\delta_c$=162.6/150.6/146.7/144.2 (quaternary C), 151.7 (C$_1$), 148.9 (C$_d$), 138.5/124.9 (C$_b$/C$_h$), 131.3 (C$_e$), 130.0 (C$_f$), 123.7 (C$_e$), 122.0 (C$_a$), 121.0 (C$_2$), 119.8 (C$_a$), 107.9 (C$_3$), 69.9 (C$_7$), 30.5 (C$_{14}$), 29.0 (C$_8$), 28.2 (C$_{12}$), 27.9 (C$_{10}$), 27.7/24.9 (C$_9$/C$_{11}$). TOF MALDI-MS(+): m/z 1029.8 [M−PF$_6$]$^+$. HRMS (ES$^+$): Calc. for C$_{50}$H$_{52}$IrN$_4$O$_4$S$_2$ 1029.3060, found 1029.3018 UV-VIS (MeCN) $\lambda_{max}$ [nm]= 255, 325, 400. UV-VIS (1% MeCN/H$_2$O) $\lambda_{max}$[nm]=255, 325, 400. Emission (MeCN, $\lambda_{exc}$=355 nm) A$_{max}$ [nm]=515 nm. Emission (1% MeCN/H$_2$O, $\lambda_{exc}$=355 nm) $\lambda_{max}$ [nm]= 565 nm.

[Ir(ppy)$_2$(PhenSH)]PF$_6$: IrPhenSH (Green)

To [Ir(ppy)$_2$(PhenSAc)]PF$_6$ (50 μL, 7.96 mM in MeCN) was added NH$_4$OH$_{(aq)}$ solution (50 μL, 30% wt). The mixture was shaken for ten min in a sealed vial to render [Ir(ppy)$_2$(PhenSH)]Cl, directly prior to titration into the colloid. TOF MALDI-MS(+): 944.2 [M−PF$_6$]$^+$ UV-VIS (MeCN) $\lambda_{max}$ [nm]=255, 325, 400

B. NANOPARTICLE PREPARATION

Citrate Au15NP[5]

All glassware was washed with aqua regia (HCl:HNO$_3$, 3:1), rinsed with deionised water and dried in an oven overnight.

HAuCl$_4$.3H$_2$O (49.85% Au) (0.0988 g, 0.2501 mmol) was dissolved in 250 ml of deionised water, and the solution was heated to reflux, with vigorous stirring. A solution of trisodium citrate (0.2858 g, 0.9718 mmol) in deionised water (25 ml water, 38.87 mM) was added rapidly to the vortex. The yellow solution slowly darkened to a deep burgundy colour, and was kept at reflux for 10 min. The solution was cooled to room temperature, with stirring for a further 15 mins to yield the citrate Au15NP. Colloids were kept at room temperature and in the dark. UV-VIS (H$_2$O) $\lambda_{max}$ in nm: 520 (SPR), 260.

Larger than 15 nm Citrate AuNP:
The method was modified from Ziegler et Eychmuller.[6]
The following stock solutions were prepared:
i. Ascorbic acid stock solution: ascorbic acid (502 mg, 2.85 mmol, 1% w/v) in water,
ii. Trisodium citrate stock solution: trisodium citrate dihydrate (500 mg, 1.70 mmol, 1% w/v) in water,
iii. Au$^{3+}$ stock solution: HAuCl$_4$.3H$_2$O (100 mg, 0.25 mmol, 0.2% w/v) water.
iv. Au15NP seeds prepared according to Grabar et al.[5]

Growth Step 1:
Au15NP (6 mL, 9 nM colloid in water) were diluted to 40 mL. All further steps were performed under stirring. Au$^{3+}$ stock solution (4 mL) was diluted to 20 mL, then added dropwise over 15 min. Ascorbic acid stock solution (1 mL) was combined with trisodium citrate stock solution (0.5 mL) and diluted to 20 mL, then added dropwise over 15 minutes to give a dark red solution. The mixture was refluxed for 30 min at 100° C.

Growth Step 2:
An aliquot of the reaction mixture (9 mL) was left to cool, then was diluted to 40 mL. Au$^{3+}$ stock solution (4 mL), diluted to 20 mL, was added dropwise over 15 min. Ascorbic acid stock solution (1 mL) and trisodium citrate stock solution (0.5 mL) were diluted to 20 mL, then added dropwise over 15 min. The mixture was refluxed at 100° C. for 30 min to render a red/purple solution.

Growth Step 3:
An aliquot of the reaction mixture (40 mL) was left to cool. Au$^{3+}$ stock solution (16 mL) was diluted to 20 mL and added dropwise to the reaction mixture over 15 min. Ascorbic acid stock (4 mL) with trisodium citrate stock (2 mL), diluted to 20 mL, were added dropwise to the mixture over 15 min to give a dark brown colloid. The mixture was refluxed for 30 min at 100° C., then allowed to cool to yield AuNP100 as a light brown colloid in water (40 pM). UV-VIS (H$_2$O) $\lambda_{max}$ [nm]=566 (SPR), 296.

The samples were characterised by dynamic light scattering measurements (intensity distribution), Transmission Electron Microscopy (TEM) and Surface Plasmon Resonance band (UV-Vis).

| Sample | Intensity Distribution | Polydispersity Index | Size by TEM | SPR |
|---|---|---|---|---|
| Seeds | 26 nm | 0.097 | 15 nm | 520 nm |
| Growth Step 1 | 45 nm | 0.311 | 25 nm | 522 nm |
| Growth Step 2 | 70 nm | 0.298 | 50 nm | 533 nm |
| Growth Step 3 | 128 nm | 0.138 | 100 nm | 566 nm |

C. COATING PROCEDURES AND CHARACTERISATION

Ru-TAu15NP

Citrate-stabilised Au15NP (200 μl, 9.4 nM, 1.99 pmol) were dissolved in deionised water (2.5 ml), and Tween 20® surfactant (1.5 ml, 2.02 mM, 3.03 pmol) was added. The solution was shaken and allowed to equilibrate at room temperature for 20 mins. Surface adsorption of the surfactant onto the NP was monitored by UV-Vis absorption spectroscopy The RuBpySH (1.01 mM) solution was titrated into the T20/Au15NP, and the UV-Vis absorption spectrum was monitored with 0-25 μl (0-9.27 μM) additions. Excess complex and surfactant were removed by size-exclusion chromatography using Sephadex (RTM) G-25 resin, eluting with deionised water, to give Ru-TAu15NP as a pink colloid, with an approximate concentration of 0.25 nM (NPs). The ratio of Ru to AuNP is approximately 2200 as calculated by UVvis and by ICP-OES (Inductively Coupled Plasma-Optical Emission Spectroscopy) The maximum concentration that can be reached with Tween 20 is 0.7 nM of Ru-TAu15NP.

Ru-ZAu15NP

In a similar procedure with the one described above we used Zonyl7950 in place of Tween20. To 1 ml of citrate-stabilised Au 15 NPs 100 μl of Zonyl 23 mM were added. The solution was shaken and allowed to equilibrate at room temperature for 20 mins. The RuBpySH (3.4 mM) solution was titrated (0-15 μl additions) into the ZonylAu15 NPs. Centrifugations was used successfully as an alternative method for removing excess of surfactant and metal complex. Coating was confirmed with UV-Vis, Transmission Electron Microscopy, ICP-OES(Inductive coupled emission spectroscopy). The final concentration of nanoparticles is Ru-Z-Au15NP 9 nM (much higher in this case rather than the TWEEN surfactant).

Ru-ZAu100NP, Ir-ZAu100NP

The coating of the larger nanoparticles i.e. Au100NP with Ir or Ru complexes followed a similar method to that described above. The final concentration of the 100 nm nanoparticles is 40 pM.

Figure 1:
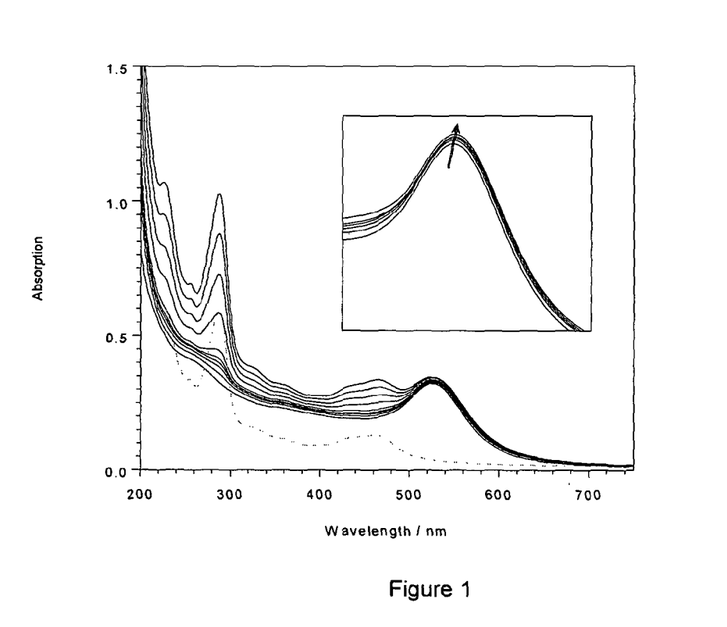
FIG. 1 is a UV-Vis absorption spectrum (solid lines) of the titration of 0-9 µM RuBpySH into 0.7 nM aqueous citrate Au15 nanoparticles in 1 mM aqueous Tween20.

The UV-Vis absorption spectrum (solid lines) of the titration of 0-9 μM RuBpySH into 0.7 nM aqueous citrate Au15 nanoparticles in 1 mM aqueous Tween20 is shown in FIG. 1 as an example of the monitoring of the coating procedure. Initially a bathochromic shift in the Surface Plasmon Resonance (SPR) is observed, until the $^1$MLCT band of the RuBpySH begins to convolute with the SPR. The dashed line indicates the UV-Vis spectrum of 9 μM RuBpySH in 1 mM aqueous TWEEN 20.

Figure 2:
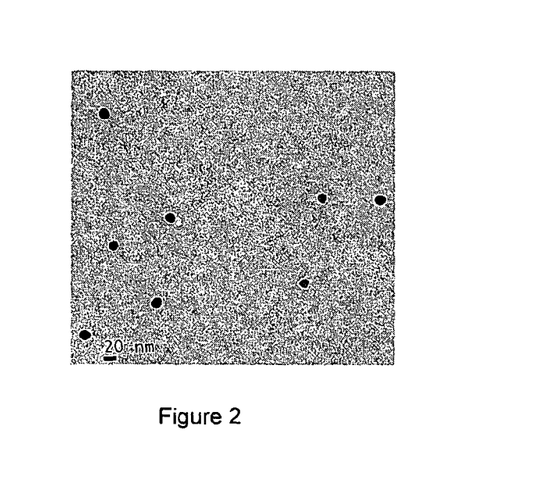
FIG. 2 is a transmission electron micrograph of purified Ru-T Au15 NPs in accordance with the invention.

A transmission electron micrograph of the purified Ru-T Au15 NPs is shown as FIG. 2. The micrograph was measured on a Jeol 1200× T E Microscope, by air-drying a 50 μL colloid drop onto formvar-coated 200-mesh copper grids. The image shows monodisperse nanoparticles with the predicted size as prepared from the Au15NPs, confirming that the coating did not alter the nanoparticle size.

Figure 3:
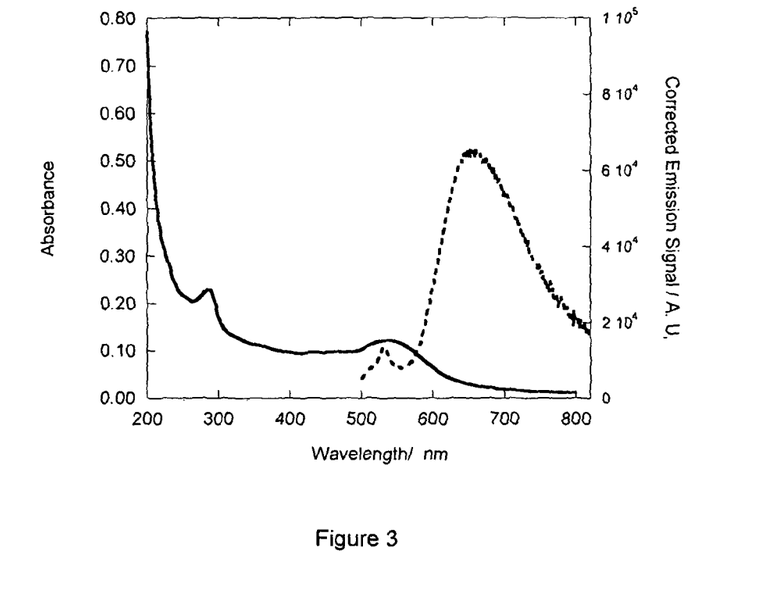
FIG. 3 is a UV-Vis Absorption spectrum (full line) and Luminescence Spectrum, $\lambda_{exc}$=450 nm, (dashed line) of 0.3 nM Ru-TAu15NP in accordance with the present invention.

FIG. 3 shows the UV-Vis Absorption spectrum (full line) and Luminescence Spectrum, $\lambda_{exc}$=450 nm, (dashed line) of 0.3 nM Ru-TAu15NP. The spectrum shows clearly the Surface Plasmon Resonance band shift indicative of nanoparticle functionalisation.

Solutions of Ir yellow nanoparticles (Ir-ZAu100NP) and Ru nanoparticles (Ru-ZAu100NP) show strong luminescence upon excitation with a simple hand-held TLC UV-vis lamp the Ir-ZAL100NP glowed bright yellow and the Ru-ZAu100NP glowed red.

Figure 4:
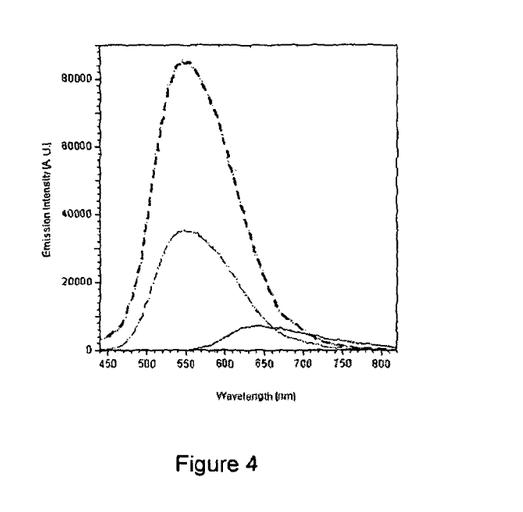
FIG. 4 shows Luminescence Spectra of Ru-ZAu100NP $\lambda_{exc}$=450 nm (solid line) and Ir-ZAu100NP $\lambda_{exc}$=355 nm (bold dotted line) and Ir-ZAu100NP $\lambda_{exc}$=405 nm (dotted line)

The luminescence spectra of Ru-ZAu100NP and Ir-ZAu100NP are presented for comparison in FIG. 4 from which it can be seen the spectrum for of Ru-ZAu100NP $\lambda_{exc}$=450 nm (solid line) and the spectra for Ir-ZAu100NP $A_{exc}$=355 nm (bold dotted line) and $\lambda_{exc}$=405 nm (dotted line).

The following lifetime measurements were taken with a 445 nm laser, and fitted with a tail exponential. All fits had $\chi^2$ values between 1.00 and 1.30.

| Moiety | Aerated τ/ns | Degassed τ/ns |
|---|---|---|
| RuBpySH in 1% MeCN/water | 245 | 324 |
| RuBpySH in 1% MeCN/aqueous surfactant | 382 | 452 |
| Ru-TAu15NP | 300 | 360 |
| Ru-ZAu100NP | 402 | 602 |
| IrBpySH (1% MeCN/Water) | 37 (29%), 233 (71%) | 22 (35%), 243 (65%) |
| Ir-ZAu100 NP | 94 (8%), 287 (92%) | 230 (14%), 656 (86%) |

It can be seen that the lifetimes of the RuBpySH and IrBpySH (yellow) complexes are not quenched by the AuNP upon attachment. In fact, it increases, perhaps due to the immobilisation reducing the rate of non-radiative decay paths via high energy vibrational modes, and/or by reducing $^3O_2$ quenching.

Calculation of the Coverage of the NPs with RuBpySH:

The nanoparticles are centrifuged, the supernatant is decanted, and the pellet is re-suspended 3 times to remove excess surfactant and metal complex.

| Size | Ratio of RuBpySH complexes per AuNP |
|---|---|
| Ru-ZAu15NP | 2300 |
| Ru-ZAu25NP | 4350 |
| Ru-ZAu50NP | 31,500 |
| Ru-ZAu100NP | 107,000 |

The Zonyl 7950 polymer allows higher concentrations of nanoparticles to be formed without aggregation.

D. COATING AUNP WITH MRI ACTIVE (GDSH) AND LUMINESCENT METAL Complexes (RuBpySH) for Multimodal Imaging: RuGd-Au15NP Citrate-stabilised Au15NP were coated with GdSH complex (RMM=761)[7] first, and then RuBpySH was added. A 3.97 mM solution of GdSH in MeOH was titrated into 4.7 nM CNPs.

GdSH

Titration of GdSH into 4.7 nM Au15NP gave a 5.5 nm bathochromic in the SPR band of the CNPs, and reached a plateau in the binding curve upon addition of 52 mM of the complex, indicating a saturation of this binding event. The subsequent addition of RuBpySH did not lead to immediate aggregation, but rather a further bathochromic shift in the SPR band of 3 nm. (FIG. 5, panel a).

Figure 5:
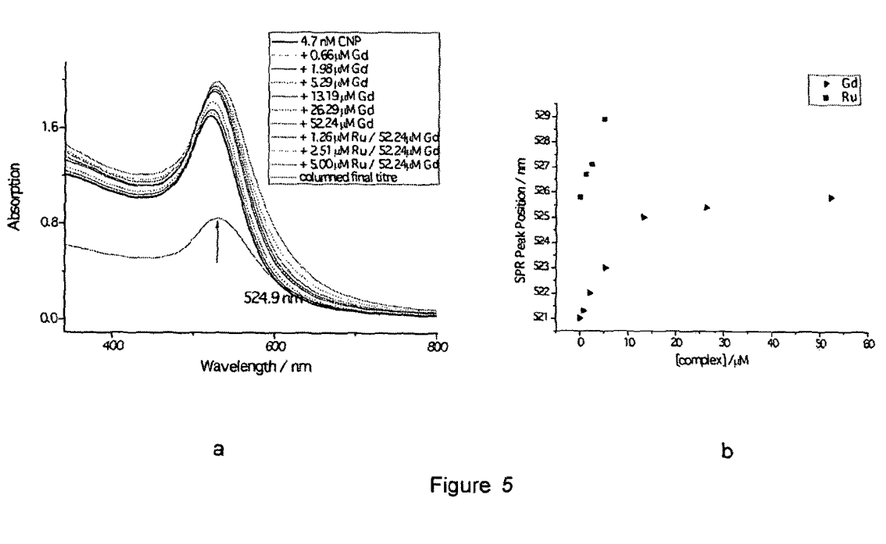
FIG. 5 shows (a) the UV-Vis Absorption Spectrum of a titration of GdSH and RuBpySH into aqueous citrate-stabilised Au NPs and (b) a plot of the SPR peak position vs concentration of each complex

The titre was purified by size-exclusion chromatography, and the purified functionalised colloid, RuGd-Au15NP gave the UV-Vis absorption spectrum shown by the arrow in panel a of FIG. 5. The luminescence spectra show the characteristic ruthenium signal as shown in the other examples. The estimated concentration of this is 2 nM (NPs). The plot of the SPR peak position vs concentration of each complex is shown in panel b.

The Transition Electron Micrograph of RuGd-Au15NP confirms that the size of the nanoparticles is unchanged by the addition of the complexes, demonstrating that the particles have not aggregated during the coating process.

These results are consistent with the dual coverage of the nanoparticles by both Ru and Gd. In a similar method to the one presented above the surfactant can be used to change the ratio of Ru to Gd. For example to increase the Ru:Gd ratio thereby making the nanoparticles more luminescent.

E. IMAGING IN CANCER CELLS

A549 human lung carcinoma cells were separately incubated with Ru-TAu15NP, Ru-ZAu100NP and the Ir-ZAu100NP for 24 hours. The treated cells were imaged with (a) bright field and (b) epiluminescence microscopy, $\lambda_{exc}$=450 nm and the emission spectra collected. The emission spectra clearly show uptake of the NPs in the cells. Most strikingly, the luminescence of Ir-ZAu100NP was visible by eye under the microscope, a behaviour not observed by any other type of nanoparticle investigated.

To further investigate the localisation of the nanoparticles, treated cells were imaged by confocal luminescence and confocal reflectance microscopy. Confocal luminescence spectroscopy enables the imaging of luminescence in a defined focal plane. Confocal reflectance microscopy images the correspondent light scattering by the metal centres. To determine the localisation of the NP within the cell, treated cells were co-stained with Hoechst stain. In confocal luminescence microscopy, images are taken in two channels simultaneously: a blue channel for the Hoechst dye ($\lambda_{exc}$=405 nm LASER, $\lambda_{em}$=410-460 nm) and a channel for the nanoparticles, red for Ru-ZAuNP ($\lambda_{exc}$=405 nm LASER, $\lambda_{em}$=580-770 nm) and yellow for Ir-ZAuNP ($\lambda_{exc}$=405 nm LASER, $\lambda_{em}$=480-500 nm.

An overlay of the images for both types of nanoparticles shows the co-localisation of the luminescence with the bright scattering spots, confirming that the luminescent complexes are still attached to the AuNP after internalisation.

To determine the efficiency of cell uptake of the nanoparticles we have performed flow cytometry studies on Ru-ZAu100NP and shown that almost 100% of cells have been labelled with Ru-ZAu100NP.

Investigation on the coated nanoparticles in blood flow have been undertaken, to examine flow patterns. An overlay of time frames (imaging at 30 frames s$^{-1}$) of consecutive luminescence images of Ir-ZAu100NP flowing in 0% hematocrit and 30% hematocrit blood within a 100 μm ibidi channel at a 5 μL min$^{-1}$ flow rate, at 5 μm channel depth, clearly demonstrate that flow of the nanoparticles in blood can be monitored.

REFERENCES

1. Y.-R. Hong and C. B. Gorman, *The Journal of Organic Chemistry*, 2003, 68, 9019-9025.
2. S. Farabi and Z. Pikramenou, manuscript in preparation, 2011.
3. J. A. Faiz, Ph D. Thesis, University of Birmingham, 2005.
4. S. Sprouse, K. A. King, P. J. Spellane and R. J. Watt, JACS, 1984, 106, 6647.
5. K. C. Grabar, R. G. Freeman, M. B. Hommer and M. J. Natan, *Analytical Chemistry*, 1995, 67, 735-743.
6. C. Ziegler and A. Eychmuller, JPCC, 2011, 115, 4502.
7. D. J. Lewis, P. B. Glover, M. C. Solomons and Z. Pikramenou *J. Am. Chem. Soc.*, 2011, 133, 1033-1043.

The invention claimed is:

1. A composition comprising nanoparticles of a noble metal, wherein the noble metal is functionalised with at least one type of metal complex and surfactant, and wherein each nanoparticle has a loading of at least 500 and the surfactant is a fluorinated polyether wherein the metal complex is a complex of a d-block, p-block or rare earth metal, and wherein the metal complex is luminescent, radioactive or MRI active, or has anti-cancer activity.

2. The composition of claim 1, wherein each nanoparticle is 3 to 500 nm in diameter.

3. The composition of claim 1, wherein the metal complex is a complex of boron, ruthenium, iridium, osmium, zinc or gadolinium.

4. The composition of claim 1, wherein the noble metal is selected from palladium, silver, platinum and gold.

5. The composition of claim 1, wherein the metal complex comprises at least one ligand selected from a diimine.

6. The composition of claim 1, wherein the metal complex comprises from one to three ligands independently selected from bipyridines and phenanthrolines.

7. The composition of claim 1, wherein the metal complex comprises three ligands independently selected from those of formula (I) and (II):

(I)

(III)

(II)

where n=0, 1, 2, 3, or 4; p=0, 1, 2, or 3; and q=0, 1, or 2; and each R is selected from $C_1$-$C_{10}$ alkyl (including cycloalkanyl), $C_2$-$C_{10}$ alkenyl, or $C_2$-$C_{10}$ alkynyl, optionally substituted with up to 3 groups selected from amino, hydroxyl, $C_1$-$C_4$ ether, thiol, $C_1$-$C_4$ thioether, nitro, nitrile, carboxylate, $C_1$-$C_4$ ester, phenyl, pyridinyl, pyrimidinyl, furanyl, pyrrolyl, thiophenyl, imidazolyl, and thiazolyl;

provided that the complex comprises at least one ligand having at least one thiol group.

8. The composition of claim 1, wherein the metal complex comprises at least one ligand of structure (III):

9. The composition of claim 1 comprising nanoparticles functionalised with more than one type of metal complex.

10. The composition of claim 9, wherein one type of metal complex is luminescent and a second type of metal complex is MRI active.

11. A method of producing marked biomolecules or cells, the method comprising incubating the biomolecules or cells with the composition of claim 1 such that the nanoparticles label the biomolecules or are incorporated into the cells.

12. The method of claim 11, wherein the biomolecules or cells are incubated with the composition of claim 1 for 24 hours.

13. The method of claim 11, wherein the method further comprises imaging the marked biomolecules or cells.

14. The method of claim 13, wherein the marked cells are stained prior to imaging.

15. The method of claim 11, further comprising introducing the marked biomolecules or cells into a blood flow and monitoring the flow of said marked biomolecules or cells in blood.

16. The composition of claim 1, wherein the composition is a solution having a concentration of unagglomerated functionalised nanoparticles of at least 1 nM.

* * * * *